(12) United States Patent
Meyer et al.

(10) Patent No.: US 8,944,597 B2
(45) Date of Patent: Feb. 3, 2015

(54) STANDARDIZED DISPLAY OF OPTICAL COHERENCE TOMOGRAPHY IMAGING DATA

(71) Applicant: Carl Zeiss Meditec, Inc., Dublin, CA (US)

(72) Inventors: Scott A. Meyer, Livermore, CA (US); Paul F. Stetson, Piedmont, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 84 days.

(21) Appl. No.: 13/740,875

(22) Filed: Jan. 14, 2013

(65) Prior Publication Data

US 2013/0188132 A1   Jul. 25, 2013

Related U.S. Application Data

(60) Provisional application No. 61/588,548, filed on Jan. 19, 2012.

(51) Int. Cl.
*A61B 3/14* (2006.01)
*A61B 3/10* (2006.01)
*G06T 19/00* (2011.01)

(52) U.S. Cl.
CPC . *A61B 3/14* (2013.01); *A61B 3/102* (2013.01); *G06T 19/00* (2013.01); *G06T 2219/008* (2013.01)
USPC ............ 351/206; 351/200; 351/205; 351/210

(58) Field of Classification Search
CPC ...... A61B 3/10; A61B 3/1015; A61B 3/1025; A61B 3/117; A61B 3/1173; A61B 3/12; A61B 3/1208; A61B 3/1225; A61B 3/102; A61B 3/13; A61B 3/132; A61B 3/135; A61B 3/14; A61B 3/145; A61B 3/15; A61B 3/152; A61B 3/154; A61B 3/156; A61B 3/158
USPC .......................... 351/206, 210, 205, 200, 246
See application file for complete search history.

(56) References Cited

U.S. PATENT DOCUMENTS

| | | | |
|---|---|---|---|
| 5,321,501 | A | 6/1994 | Swanson et al. |
| 6,266,452 | B1 | 7/2001 | McGuire |
| 6,546,272 | B1 | 4/2003 | MacKinnon et al. |
| 6,771,736 | B2 | 8/2004 | Sabol et al. |
| 6,934,698 | B2 | 8/2005 | Judd et al. |

(Continued)

OTHER PUBLICATIONS

Ajtony et al., "Relationship between Visual Field Sensitivity and Retinal Nerve Fiber Layer Thickness as Measured by Optical Coherence Tomography", Investigative Ophthalmology & Visual Science, vol. 48, No. 1, Jan. 2007, pp. 258-263.

(Continued)

*Primary Examiner* — Ricky Mack
*Assistant Examiner* — William Alexander
(74) *Attorney, Agent, or Firm* — Morrison & Foerster LLP

(57) ABSTRACT

Systems and methods for efficiently displaying large volumes of medical imaging data using pre-defined dynamic displays to illustrate key anatomic features are described. In a preferred embodiment, one or more pulse files comprising en face images of sub sections of the volume are displayed sequentially to the user in a playback loop. These displays can aid in navigation of data for review and future data acquisition. Additional images generated from the data can be displayed next to or overlaid on the pulse files.

25 Claims, 2 Drawing Sheets

(56) References Cited

U.S. PATENT DOCUMENTS

| | | | |
|---|---|---|---|
| 7,015,907 | B2 | 3/2006 | Tek et al. |
| 7,020,313 | B2 | 3/2006 | Declerck et al. |
| 7,050,615 | B2 | 5/2006 | Avinash et al. |
| 7,084,128 | B2 | 8/2006 | Yerxa et al. |
| 7,301,644 | B2 | 11/2007 | Knighton et al. |
| 7,347,548 | B2 | 3/2008 | Huang et al. |
| 7,401,921 | B2 | 7/2008 | Baker et al. |
| 7,566,128 | B2 | 7/2009 | Tsukada et al. |
| 7,641,338 | B2 | 1/2010 | Fukuma et al. |
| 7,668,342 | B2 | 2/2010 | Everett et al. |
| 7,768,652 | B2 | 8/2010 | Everett |
| 7,782,464 | B2 | 8/2010 | Mujat et al. |
| 8,045,176 | B2 | 10/2011 | Everett et al. |
| 8,223,143 | B2 | 7/2012 | Dastmalchi et al. |
| 8,332,016 | B2 | 12/2012 | Stetson |
| 2003/0164860 | A1 | 9/2003 | Shen et al. |
| 2004/0027359 | A1 | 2/2004 | Aharon et al. |
| 2005/0238253 | A1 | 10/2005 | Behrenbruch et al. |
| 2006/0030768 | A1 | 2/2006 | Ramamurthy et al. |
| 2006/0119858 | A1 | 6/2006 | Knighton et al. |
| 2006/0184014 | A1 | 8/2006 | Pfeiler |
| 2006/0187462 | A1 | 8/2006 | Srinivasan et al. |
| 2007/0025642 | A1 | 2/2007 | Buckland et al. |
| 2007/0070295 | A1 | 3/2007 | Tsukada et al. |
| 2007/0115481 | A1 | 5/2007 | Toth et al. |
| 2007/0216909 | A1 | 9/2007 | Everett et al. |
| 2007/0222946 | A1 | 9/2007 | Fukuma et al. |
| 2007/0291277 | A1 | 12/2007 | Everett et al. |
| 2009/0244485 | A1* | 10/2009 | Walsh et al. .................. 351/221 |
| 2010/0073633 | A1* | 3/2010 | Uchida et al. ................. 351/206 |
| 2010/0079580 | A1 | 4/2010 | Waring, IV |
| 2010/0128943 | A1 | 5/2010 | Matsue et al. |
| 2011/0109631 | A1 | 5/2011 | Kunert et al. |
| 2011/0299034 | A1* | 12/2011 | Walsh et al. .................. 351/206 |
| 2012/0249956 | A1 | 10/2012 | Narasimha-Iyer et al. |
| 2013/0181976 | A1 | 7/2013 | Dastmalchi et al. |

OTHER PUBLICATIONS

Bengtsson et al., "A New Generation of Algorithms for Computerized Threshold Perimetry, SITA", Acta Ophthalmologica Scandinavica, vol. 75, 1997, pp. 368-375.

Budenz et al., "Reproducibility of Retinal Nerve Fiber Thickness Measurements Using the Stratus OCT in Normal and Glaucomatous Eyes", Investigative Ophthalmology & Visual Science, vol. 46, No. 7, Jul. 2005, pp. 2440-2443.

Budenz et al., "Sensitivity and Specificity of the StratusOCT for Perimetric Glaucoma", Ophthalmology, vol. 112, No. 1, Jan. 2005, pp. 3-9.

Chang et al., "New Developments in Optical Coherence Tomography for Glaucoma", Current Opinion in Ophthalmology, vol. 19, 2008, pp. 127-135.

Dastmalchi et al., Unpublished U.S. Appl. No. 14/245,910, filed Apr. 4, 2014, titled "User Interface for Efficiently Displaying Relevant Oct Imaging Data".

El Beltagi et al., "Retinal Nerve Fiber Layer Thickness Measured with Optical Coherence Tomography Is Related to Visual Function in Glaucomatous Eyes", Ophthalmology, vol. 110, No. 11, Nov. 2003, pp. 2185-2191.

Gardiner et al, "Evaluation of the Structure-Function Relationship in Glaucoma", Investigative Ophthalmology & Visual Science, vol. 46, No. 10, Oct. 2005, pp. 3712-3717.

Harwerth et al., "Linking Structure and Function in Glaucoma", Progress in Retinal and Eye Research, 2010, pp. 1-23.

Hougaard et al., "Glaucoma Detection by Stratus OCT", J. Glaucoma, vol. 16, No. 3, May 2007, pp. 302-306.

Julia et al., Unpublished U.S. Appl. No. 14/199,874, filed Mar. 6, 2014, titled "Oct Acquisition and User Interface", 23 pages.

Leung et al., "Comparative Study of Retinal Nerve Fiber Layer Measurement by StratusOCT and GDx VCC, II: Structure/Function Regression Analysis in Glaucoma", Investigative Ophthalmology & Visual Science, vol. 46, No. 10, Oct. 2005, pp. 3702-3711.

Paunescu et al., "Reproducibility of Nerve Fiber Thickness, Macular Thickness, and Optic Nerve Head Measurements Using StratusOCT", Investigatative Ophthalmology & Visual Science, vol. 45, No. 6, Jun. 2004, pp. 1716-1724.

Sato et al., "Correlation Between Retinal Nerve Fibre Layer Thickness and Retinal Sensitivity", Acta Ophthalmologica, vol. 86, 2008, pp. 609-613.

Schuman et al., "Reproducibility of Nerve Fiber Layer Thickness Measurements Using Optical Coherence Tomography", Ophthalmology, vol. 103, No. 11, Nov. 1996, pp. 1889-1898.

Sommer et al., "Clinically Detectable Nerve Fiber Atrophy Precedes the Onset of Glaucomatous Field Loss", Arch Ophthalmol., vol. 109, Jan. 1991, pp. 77-83.

Choma et al., "Sensitivity Advantage of Swept Source and Fourier Domain Optical Coherence Tomography", Optics Express, vol. 11, No. 18, Sep. 8, 2003, pp. 2183-2189.

Haeker et al., "Use of Varying Constraints in Optimal 3-D Graph Search for Segmentation of Macular Optical Coherence Tomography Images", MICCAI, vol. 10, part-1, 2007, pp. 244-251.

Huang et al., "Optical Coherence Tomography", Science, vol. 254, Nov. 22, 1991, pp. 1178-1181.

Jiao et al., "Simultaneous Acquisition of Sectional and Fundus Ophthalmic Images with Spectral-Domain Optical Coherence Tomography", Optics Express, vol. 13 No. 2, Jan. 24, 2005, pp. 444-452.

Lee et al., "In vivo Optical Frequency Domain Imaging of Human Retina and Choroid", Optics Express, vol. 14, No. 10, May 15, 2006, pp. 4403-4411.

Leitgeb et al., "Ultrahigh Resolution Fourier Domain Optical Coherence Tomography", Optics Express, vol. 12, No. 10, May 17, 2004, pp. 2156-2165.

Nassif et al., "In vivo Human Retinal Imaging by Ultrahigh-Speed Spectral Domain Optical Coherence Tomography", Optics Letters, vol. 29, No. 5, Mar. 1, 2004, pp. 480-482.

Tan et al., "Detection of Macular Ganglion Cell Loss in Glaucoma by Fourier-Domain Optical Coherence Tomography", Ophthalmology, vol. 116, No. 12, Dec. 2009, pp. 2305-2314.e2.

Wojtkowski et al., "Three-Dimensional Retinal Imaging with High-Speed Ultrahigh-Resolution Optical Coherence Tomography", Ophthalmology, vol. 112, No. 10, Oct. 2005, pp. 1734-1746.

Zawadzki et al., "Adaptation of a Support Vector Machine Algorithm for Segmentation and Visualization of Retinal Structures in Volumetric Optical Coherence Tomography Data Sets", Journal of Biomedical Optics, vol. 12, No. 4, Jul./Aug. 2007, pp. 041206-1-8.

Final Office Action received for U.S. Appl. No. 13/549,370, mailed on Jan. 6, 2014, 14 pages.

Non Final Office Action received for U.S. Appl. No. 11/978,184, mailed on Jul. 18, 2011, 19 pages.

Final Office Action received for U.S. Appl. No. 11/978,184, mailed on Jan. 10, 2012, 23 pages.

Notice of Allowance received for U.S. Appl. No. 11/978,184, mailed on Mar. 20, 2012, 14 pages.

Notice of Allowance received for U.S. Appl. No. 11/978,184, mailed on May 10, 2012, 4 pages.

Non Final Office Action received for U.S. Appl. No. 13/549,370, mailed on Jul. 2, 2013, 12 pages.

Bashkansky et al., "Statistics and Reduction of Speckle in Optical Coherence Tomography", Optics Letters, vol. 25, No. 8, Apr. 15, 2000, pp. 545-547.

Carpineto et al., "Custom Measurement of Retinal Nerve Fiber Layer Thickness Using Stratus OCT in Normal Eyes", European Journal of Ophthalmology vol. 15, No. 3, 2005, pp. 360-366.

De Boer et al., "Improved Signal-to-Noise Ratio in Spectral-Domain Compared with Time-Domain Optical Coherence Tomography", Optics Letters, vol. 28, No. 21, Nov. 1, 2003, pp. 2067-2069.

Frangi et al., "Model-Based Quantitation of 3-D Magnetic Resonance Angiographic Images", IEEE Transactions on Medical Imaging, vol. 18, No. 10, Oct. 1999, pp. 946-956.

Frangi et al., "Multiscale Vessel Enhancement Filtering", Lecture Notes in Computer Science, vol. 1496, 1998, pp. 130-137.

Gerig et al., "Nonlinear Anisotropic Filtering of MRI Data", IEEE Transactions on Medical Imaging, vol. 11, No. 2, Jun. 1992, pp. 221-232.

(56) References Cited

OTHER PUBLICATIONS

Hausler et al., "'Coherence Radar' and 'Spectral Radar'—New Tools for Dermatological Diagnosis", Journal of Biomedical Optics, vol. 3, No. 1, Jan. 1998, pp. 21-31.

Ishikawa et al., "Macular Segmentation with Optical Coherence Tomography", Investigative Ophthalmology & Visual Science, vol. 46, No. 6, 2005, pp. 2012-2017.

Leitgeb et al., "Performance of Fourier Domain Vs Time Domain Optical Coherence Tomography", Optics Express vol. 11, No. 8, Apr. 21, 2003, pp. 889-894.

Maintz et al., "A Survey of Medical Image Registration", Medical Image Analysis, vol. 2, No. 1, 1998, pp. 1-36.

Maurer et al., "A Review of Medical Image Registration", Vanderbilt University, Nashville, Tennessee 37235, Jan. 28, 1993, pp. 1-49.

Pal et al., "A Review on Image Segmentation Techniques", Pattern Recognition, vol. 26, No. 9, 1993, pp. 1277-1294.

Perona et al., "Scale-Space and Edge Detection Using Anisotropic Diffusion", IEEE Transaction on Pattern Analysis and Machine Intelligence, vol. 12, No. 7, Jul. 1990, pp. 629-639.

Podoleanu et al., "Combined Multiplanar Optical Coherence Tomography and Confocal Scanning Ophthalmoscopy", J. Biomed. Optics, vol. 9, No. 1, 2004, pp. 86-93.

Podoleanu et al., "Transversal and Longitudinal Images From the Retina of the Living Eye Using Low Coherence Reflectometry", J. Biomed. Optics, vol. 3, 1998, pp. 12-20.

Sato et al., "Three-Dimensional Multi-Scale Line Filter for Segmentation and Visualization of Curvilinear Structures in Medical Images", Medical Image Analysis, vol. 2, No. 2, 1998, pp. 143-168.

Schmitt et al., "Speckle in Optical Coherence Tomography", Journal of Biomedical Optics, vol. 4, No. 1, Jan. 1999, pp. 95-105.

Vermeer et al., "A Model Based Method for Retinal Blood Vessel Detection", Computers in Biology and Medicine, vol. 34, 2004, pp. 209-219.

Yanuzzi et al., "Ophthalmic Fundus Imaging: Today and Beyond", American Journal of Opthalmoscopy, vol. 137, No. 3, Mar. 2004, pp. 511-524.

Yu et al., "Speckle Reducing Anisotropic Diffusion", IEEE Transactions on Image Processing, vol. 11, No. 11, Nov. 2002, pp. 1260-1270.

Zana et al., "A Multimodal Registration Algorithm of Eye Fundus Images Using Vessels Detection and Hough Transform", IEEE Transactions on Medical Imaging, vol. 18, No. 5, May 1999, pp. 419-428.

Dastmalchi et al., U.S. Appl. No. 13/549,370, titled "User Interface for Efficiently Displaying Relevant Oct Imaging Data", filed on Jul. 13, 2012.

Hitzenberger et al., "Three-Dimensional Imaging of the Human Retina by High-Speed Optical Coherence Tomography", Optics Express, vol. 11, No. 21, Oct. 20, 2003, pp. 2753-2761.

\* cited by examiner

STANDARDIZED DISPLAY OF OPTICAL COHERENCE TOMOGRAPHY IMAGING DATA

PRIORITY

The following application claims priority to U.S. Provisional Application Ser. No. 61/588,548 filed Jan. 19, 2012, hereby incorporated by reference.

FIELD OF THE INVENTION

The present invention relates to optical medical imaging, and in particular to the display of large volumes of optical coherence tomography imaging data of the human eye.

BACKGROUND

Optical Coherence Tomography (OCT) is a technique for performing high-resolution cross-sectional imaging that can provide images of tissue structure on the micron scale in situ and in real time (Huang et al. "Optical Coherence Tomography" Science 254(5035):1178 1991). OCT is a method of interferometry that determines the scattering profile of a sample along the OCT beam. Each scattering profile is called an axial scan, or A-scan. Cross-sectional images (B-scans), and by extension 3D volumes, are built up from many A-scans, with the OCT beam moved to a set of transverse locations on the sample. OCT provides a mechanism for micrometer resolution measurements.

In frequency domain OCT (FD-OCT), the interferometric signal between light from a reference and the back-scattered light from a sample point is recorded in the frequency domain rather than the time domain. After a wavelength calibration, a one-dimensional Fourier transform is taken to obtain an A-line spatial distribution of the object scattering potential. The spectral information discrimination in FD-OCT is typically accomplished by using a dispersive spectrometer in the detection arm in the case of spectral-domain OCT (SD-OCT) or rapidly scanning a swept laser source in the case of swept-source OCT (SS-OCT).

Evaluation of biological materials using OCT was first disclosed in the early 1990's (see for example U.S. Pat. No. 5,321,501). Frequency domain OCT techniques have been applied to living samples (see for example Nassif et al. "In vivo human retinal imaging by ultrahigh-speed spectral domain optical coherence tomography" Optics Letters 29(5): 480 2004). The frequency domain techniques have significant advantages in speed and signal-to-noise ratio as compared to time domain OCT (see for example Choma, M. A., et al. "Sensitivity advantage of swept source and Fourier domain optical coherence tomography" Optics Express 11(18): 2183 2003). The greater speed of modern OCT systems allows the acquisition of larger data sets, including 3D volume images of human tissue.

Improvements in imaging displays frequently accompany improvements in data acquisition methods and devices. For example, development of higher resolution imaging devices creates a need or motivation for higher resolution imaging displays; faster 2-D data acquisition increases the need for high speed data transmission and storage and motivates improvements in 3-D display applications; improvements in the signal to noise ratio in acquired data stimulates new uses and displays for that information.

Large medical imaging data sets, such as those acquired during volumetric OCT imaging, present difficulties in displaying relevant information to operators/users. Medical practitioners need to obtain relevant information quickly in a format that can be efficiently processed. A traditional approach to displaying 3-D volumes is multi-planar reconstruction, which simultaneously displays images from different viewing angles. The user then "scrolls" through the volume looking for relevant images. An alternative approach utilizes modern computational power to identify features of interest and present these to the user through volume rendering. Many times, an expert user benefits from observing individual slices of the image data directly. However, selection of these images can be time-consuming and there is a need to improve the means for accessing relevant slices. Herein, a volume slice will generally refer to planar data extracted from a volume, while B-scan will refer to a planar section of the volume that was acquired sequentially. In this sense, a B-scan is a slice, while a slice may be a B-scan. However, the terms are often used interchangeably in the literature and the distinction is often not relevant, since a slice could have been a B-scan under an alternative scanning sequence.

SUMMARY

It is an object of the present invention to provide systems and methods for reviewing 3D medical data, such as OCT data, using pre-defined dynamic displays to illustrate key anatomic features in the tissue, and providing tools to further investigate regions of interest. This could be used in multiple clinical settings including offices, clinics, and surgical theaters when the OCT is integrated into a surgical microscope. The invention takes advantage of electronic review devices at the point of care to provide rapid and automated review of data and navigation of 3D data sets.

The display creates a navigation system to allow doctors to quickly review a 3D data set by passively and quickly observing clinically relevant visualizations. Prior approaches performed this function with either static thickness maps or manually controlled en-face "slab" images. This approach combines the speed and simplicity of static maps with the richness of en-face slab images. Animated B-scan "flythroughs" and 3D visualizations, such as those described in U.S. Pat. No. 8,223,143 and implemented in the Cirrus OCT instrument (Carl Zeiss Meditec Inc. Dublin, Calif.) do not typically provide the same clinically relevant data.

DETAILED DESCRIPTION

Figure 1:
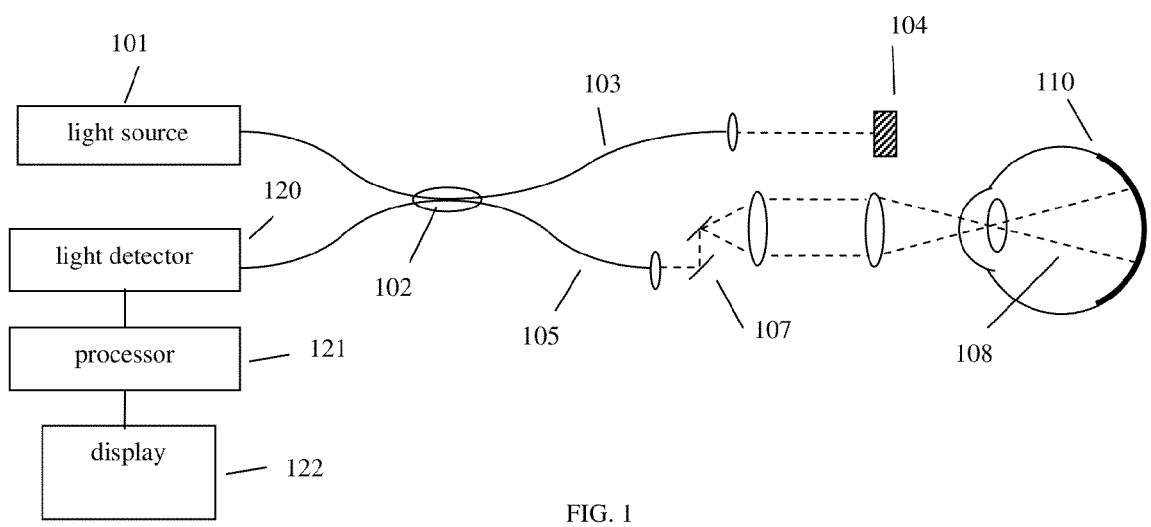
FIG. 1 illustrates the basic components of an FD-OCT system that could be used to collect data for display according to the present invention.

Various embodiments of the invention can be envisioned by one skilled in the art. The embodiments described herein are directed to the field of ophthalmology, but the basic concept could be applied in other fields as well. As demonstrated below, this concept is especially well suited to the layered structures of the human eye. The basic concept is to develop and use a standardized method to display 3-D data sets, in the preferred embodiment, OCT data sets. A basic FD-OCT system used to collect 3-D image data suitable for use with the present invention is illustrated in FIG. 1. A FD-OCT system includes a light source, 101, typical sources including but not limited to broadband light sources with short temporal coherence lengths or swept laser sources. (See for example, Wojtkowski, et al., "Three-dimensional retinal imaging with high-speed ultrahigh-resolution optical coherence tomography," *Ophthalmology* 112(10):1734 2005 or Lee et al. "In vivo optical frequency domain imaging of human retina and choroid," *Optics Express* 14(10):4403 2006)

Light from source 101 is routed, typically by optical fiber 105, to illuminate the sample 110, a typical sample being tissues at the back of the human eye. The light is scanned, typically with a scanner 107 between the output of the fiber and the sample, so that the beam of light (dashed line 108) is scanned over the area or volume to be imaged. Light scattered from the sample is collected, typically into the same fiber 105 used to route the light for illumination. Reference light derived from the same source 101 travels a separate path, in this case involving fiber 103 and retro-reflector 104. Those skilled in the art recognize that a transmissive reference path can also be used. Collected sample light is combined with reference light, typically in a fiber coupler 102, to form light interference in a detector 120. The output from the detector is supplied to a processor 130. The results can be stored in the processor or displayed on display 140. The processing and storing functions may be localized within the OCT instrument or functions may be performed on an external processing unit to which the collected data is transferred. This unit could be dedicated to data processing or perform other tasks which are quite general and not dedicated to the OCT device.

The interference causes the intensity of the interfered light to vary across the spectrum. The Fourier transform of the interference light reveals the profile of scattering intensities at different path lengths, and therefore scattering as a function of depth (z-direction) in the sample (see for example Leitgeb et al. "Ultrahigh resolution Fourier domain optical coherence tomography," Optics Express 12(10):2156 (2004)). The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system capable of collecting three-dimensional OCT data sets. The invention relates to processing and display of OCT data that can be done on the OCT instrument itself or on a separate computer or workstation to which collected OCT data is transferred either manually or over a networked connection.

The term, "pulse file," is used here to describe a short file in which a series of images from a single 3D OCT data set are displayed sequentially. The standard display would include one or more pulse files optionally linked to additional data displays. The idea behind the pulse files is to have a rapid, dynamic, standardized way to view data that requires minimal user intervention and to take advantage of the layered structure of the eye, as demonstrated below. While the pulse file could be any arbitrary length, a length of 0.5-5 seconds may be preferred. Preferably, the display rate would be about five frames (images) per second. A particular pulse file could be displayed repeatedly in a loop mode to allow for continuous viewing. The pulse files could guide navigation of larger data sets, provide a rapid overview of data, highlight abnormalities, and could be used for change analysis of a patient over time. The pulse file could be selected to span a specific partial volume or slab of interest within the 3D data volume based on input from the instrument operator, clinician reviewing the data, a priori knowledge of the location of specific disease or pathology, or prior knowledge of the patient's physiology. The pulse files would be based on one or more of a series of pre-defined parameters including the reference surface, the slab thickness profile, the slab velocity, the total display time, and the total display thickness. Pulse files can be generated for the inner limiting membrane (ILM) slab, the neural retina slab, the retinal pigment epithelial layer (RPE), the RPE and ILM combined, and the choroid among others.

The pulse files could be displayed on any number of platforms including the review screen of the OCT instrument, a review station associated with the instrument in the same clinic or in a different location, a web browser, a tablet computer, a smart phone, or a slide show (e.g. PowerPoint) file among others. The files could be used to review and analyze data and/or to guide further data acquisition.

In the simplest embodiment, the images comprising a pulse file could be a collection of c-scans, or horizontal slices, through the data volume (perpendicular to the scan depth), for a selected range of data, i.e. for a 512×512 cube of data, select the central 100 horizontal slices through the data and display them in series. Since the idea is to provide a fast display and given that images generated from single pixel values in the x-dimension can be noisy, it would be possible to integrate or bin the 100 slices into a reduced number of slices, by designating a single representative value (sum, integral, median value, average, median, etc) for a group of z-axis data points at each x and y position as described in U.S. Pat. No. 7,301,644 hereby incorporated by reference. It is believed that the number of images per pulse file should be between five and fifty. Using a frame rate of five frames per second, a five image pulse file would take one second to display. It is believed that to be useful, the pulse file should have at least five images. While the present description is focused on horizontal slices perpendicular to the scan direction, those skilled in the art would appreciate that slices along any arbitrary axis through the 3D data cube could also be generated and covered by the present invention.

In another embodiment of the present invention, a pulse file is created by first identifying a reference surface within the eye from the 3-D data set. A partial volume or slab of data is then established extending from the reference surface to a second surface that could be defined by its distance to the first surface or based on a second identified surface. The slab is divided into multiple sections. These multiple sections could be defined as fractional distances between two boundaries defining a specific layer as described in U.S. Pat. No. 8,332,016, hereby incorporated by reference. The sections could be of non-uniform thickness. In the preferred embodiment, a single intensity value is assigned for each section along the Z axis at each X/Y scanning position as described above. 2-D images are generated for each section using that representative value. The 2-D images are then displayed in sequence.

While the reference surface will generally be defined by a physical structure in the eye, the subject invention is not limited to using a physical surface. The slab of data can be defined by any mathematically defined boundary surface. The term boundary as used in the claims is intended to cover both physical and non-physical surfaces within the 3D data set.

In the case of ophthalmology, given the curved nature of the eye, planar data slices are of limited value. In this case, it may be desirable to create two-dimensional images that follow or are conformal to specific tissue layer boundaries, e.g. the inner limiting membrane (ILM), the retinal pigment epithelium (RPE), etc. As in the case of the c-slices described above, the images could be based on single pixel values for the data along the z-axis or more likely the result of processing a collection of z-axis data to generate a single representative value. The layer boundary or boundaries could be identified using any one of many known segmentation algorithms. (see for example Tan et al., "Detection of Macular Ganglion Cell Loss in Glaucoma by Fourier-Domain Optical Coherence Tomography," Ophthalmology 2009; 116(12), Haeker et al., "Use of Varying Constraints in Optimal 3-D Graph Search for Segmentation of Macular optical Coherence Tomography Images," MICCAI 2007 Presentation 438, or Zawadzki et al., "Adaptation of a support vector machine algorithm for segmentation and visualization of retinal structures in volumetric optical coherence tomography data sets," J Biomed Opt. 2007; 12(4) all hereby incorporated by reference). The segmented surface could be smoothed or fit to a smooth surface prior to processing. A reference surface could be highlighted by the instrument operator to serve as the boundary surfaces and a specific range could be specified. Alternatively the surface and range could be preset in the instrument. Here the Z-axis could be an orthogonal projection from the curved surface rather than using the OCT beam propagation axis as the Z-axis. Similar to the embodiment described above the partial volume of data could extend for a fixed distance from the reference surface or could extend to a second identified tissue boundary layer.

Figure 2:
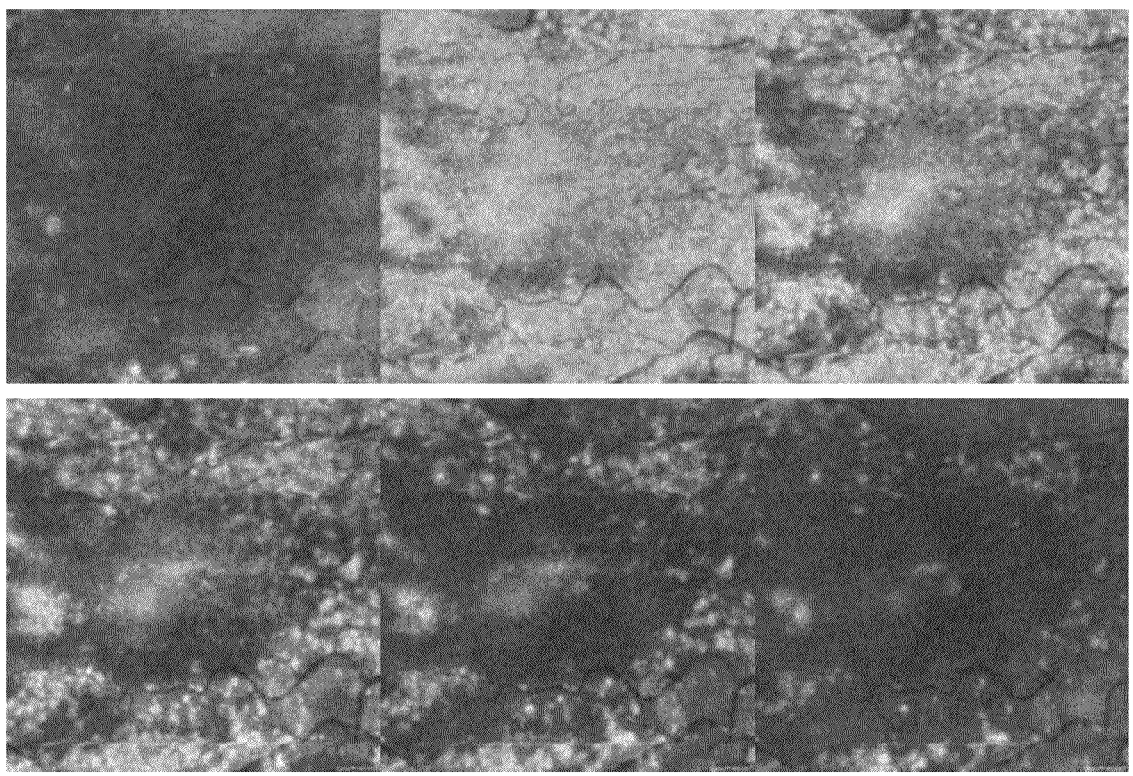
FIG. 2 shows six en face images that were generated by summing sections of data above the RPE layer that would be displayed sequentially in one aspect of the present invention.

The general idea envisioned for the preferred embodiment of the pulse file concept is illustrated in FIG. 2. A series of 6 images for a pulse file are illustrated. The images are slab images above the RPE. A cube of OCT data over the posterior of the eye including the retinal pigment epithelium (RPE) was collected. In the case illustrated in FIG. 2, a 200×200 cube was acquired. The RPE was identified using a segmentation algorithm as described above. In this case, a smooth reference surface was fit to the identified RPE layer according to the methods described in U.S. Pat. No. 7,668,342 "Method of bioimage date processing for revealing more meaningful anatomic features of diseased tissue" hereby incorporated by reference. After generating a fit to the RPE, a plurality slabs (in this case 6 slabs) of data (in this case, each slab being approximately 20 microns thick) are defined in a region extending roughly 120 microns above the RPE surface. The data at each X and Y point in each slab was summed in the z-direction. As mentioned previously the summing could occur along any axis roughly perpendicular to the identified surface and any method of generating a single representative value for the intensity data could be used instead of summing. The resulting single representative z-axis intensity values were used at each X and Y location to generate each one of the images shown in FIG. 2. The images would be displayed sequentially in a single display location on the user interface over a few seconds. The decision to select a 120 micron total thickness and divide it into 6 slabs each covering 20 microns of tissue thickness each is somewhat arbitrary. It is desirable to select a thickness for the slab that reduces noise in the data while displaying clinically meaningful information. The goal of the invention is to provide clinically helpful navigation through large quantities of data so providing displays over subsets of data that are likely to provide the clinician with insight into the health of the patient's eye is an important aspect of the invention.

A series of pulse files could be displayed together covering different regions of the eye of a patient. For instance along with the pulse file of the RPE as illustrated in FIG. 2, pulse files covering thicknesses surrounding the ILM and the choroid could be displayed simultaneously. The exact thicknesses covered and thickness of each slab image generated would depend on the particular layer but are likely to be similar to the 120 micron total thickness range and 20 micron slab thickness numbers for the RPE described above. If the choroid was being imaged with a source operating at 1 micron, the total thickness covered could be on the order of 300 microns. In some cases of clinical pathology, specific segmentations or fits to segmentations may fail. In these cases, the absence of a meaningful pulse file would also provide clinical insight and navigation to the clinician and they would focus their analysis on the pulse files created from successful segmentations or fits to segmentations.

In addition to the pulse file or files themselves, the display could contain other data that is linked to the images in the pulse file. Slice locators or lines could be displayed on the images in the pulse file indicating the locations of B-scans displayed concurrently with the pulse file. The slice locators could be adjustable by the user to change which B-scans are displayed. Other reference images like blood vessel maps or en face images generated from the 3D data set could also be displayed adjacent to or overlaid on the images in the pulse file. Multiple pulse files could be displayed at once and synchronized cursors could be used across the maps. The use of slice locators to provide guideposts to other views is disclosed in U.S. Pat. No. 8,223,143, incorporated herein by reference.

Figure 3:
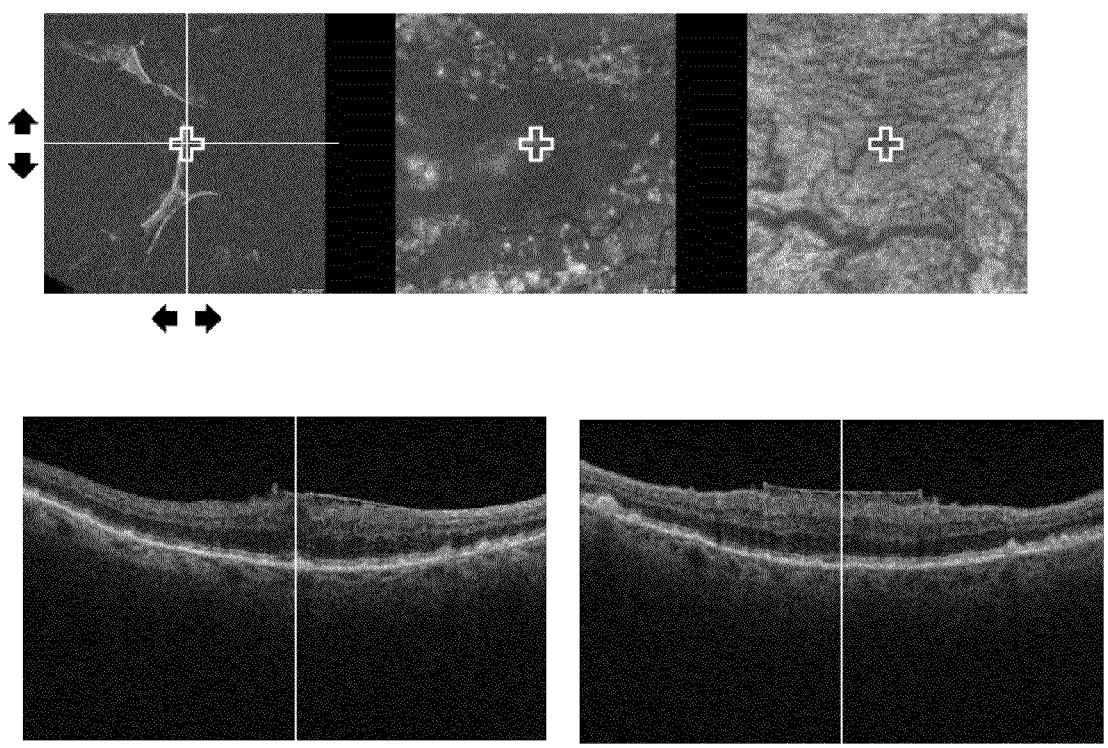
FIG. 3 illustrates one possible user interface design incorporating aspects of the present invention. The top part of the display includes three pulse files displaying loops of en face images of various layers of the retina. The bottom panel displays B-scans along the cross hairs overlaid on the pulse files.

A possible embodiment of a user interface incorporating some of these ideas is displayed in FIG. 3. The upper portion of the display contains 3 pulse files represented by static en face images. The middle pulse file contains the sequence of slabs above the RPE illustrated in FIG. 2. The left most pulse file is a file generated from a subset of OCT data surrounding the ILM and the right most pulse file is a sequence of slab images generated from a subset of data surrounding the choroid. The lines on the ILM pulse file indicate the location of the B-scans displayed on the lower portion of FIG. 3. The arrows associated with the pulse file at upper left portion of FIG. 3 indicate the ability of the clinician to adjust the B-scan displays.

Although various embodiments that incorporate the teachings of the present invention have been shown and described in detail herein, those skilled in the art can readily devise other varied embodiments that still incorporate these teachings.

The following references are hereby incorporated by reference:

Patent Literature

U.S. Pat. No. 8,223,143 Dastmalchi et al. "User interface for efficiently displaying relevant OCT imaging data"

U.S. Pat. No. 7,301,644 Knighton et al. "Enhanced optical coherence tomography for anatomical mapping"

U.S. Pat. No. 7,668,342 Everett et al. "Method of bioimage data processing for revealing more meaningful anatomic features of diseased tissue"

U.S. Pat. No. 8,045,176 Everett et al. "Methods for mapping tissue with optical coherence tomography data."

U.S. Pat. No. 7,347,548 Huang et al. "Method and apparatus for measuring a retinal sublayer characteristic"

U.S. Patent Publication No. 2004/0027359 Aharon et al. "System and method for generating movie loop display from medical image data"

U.S. Pat. No. 7,782,464 Mujat et al. "Processes, arrangements and systems for providing a fiber laser thickness map based on optical coherence tomography images"

US Patent Publication No. 2010/0079580 Waring et al. "Apparatus and method for biomedical imaging"

U.S. Pat. No. 6,934,698 Judd et al. "Medical image management system"

US Patent Publication No. 2010/0128943 Matsue et al. "Medical image generation apparatus, medical image storage apparatus, medical image display apparatus, and medical image display system"

US Patent Publication No. 2011/0109631 Kunert et al. "System and method for performing volume rendering using shadow calculation"

U.S. Pat. No. 8,332,016 Stetson et al. "Non-linear projections of 3-D medical imaging data"

Non-Patent Literature

Jiao et al., "Simultaneous acquisitions of sectional and fundus ophthalmic images with spectral-domain optical coherence tomography" Optics Express 13(2) 444-452 2005.

Tan et al., "Detection of Macular Ganglion Cell Loss in Glaucoma by Fourier-Domain Optical Coherence Tomography," Ophthalmology 2009; 116(12)

Haeker et al., "Use of Varying Constraints in Optimal 3-D Graph Search for Segmentation of Macular optical Coherence Tomography Images," MICCAI 2007 Presentation 438, Zawadzki et al., "Adaptation of a support vector machine algorithm for segmentation and visualization of retinal structures in volumetric optical coherence tomography data sets," J Biomed Opt. 2007; 12(4)

What is claimed is:

1. A method of displaying 3-D image data of an eye of a patient acquired with an optical coherence tomography (OCT) system, said system including a radiation beam that is scanned in X and Y directions over the eye and generating a 3-D data set corresponding to the distribution of reflection sites within the eye, said method comprising:
    identifying a reference surface within the eye from the 3-D data set;
    dividing the data into multiple sections ranging from the reference surface along a Z axis roughly perpendicular to one of the X and Y scanning directions or the reference surface;
    for each section, assigning a single intensity value at each of a plurality of X and Y positions representative of the data along the Z-axis;
    generating a 2-D image of the single representative values for each section; and
    displaying the generated 2-D images sequentially.

2. A method as recited in claim 1, wherein the reference surface is identified by segmenting layers in the retina.

3. A method as recited in claim 2, wherein the reference surface is the ILM and the selected range extends towards the RPE.

4. A method as recited in claim 2, wherein the reference surface is the RPE and the selected range extends into the choroid.

5. A method of displaying 3-D image data of an eye of a patient acquired with an optical coherence tomography (OCT) system, said system including a radiation beam that is scanned over the eye and generating a 3-D data set corresponding to the distribution of reflection sites within the eye, said method comprising:
    defining a region of data between two spaced apart boundaries within the 3D set;
    dividing the region into a plurality of slabs of data extending between the boundaries;
    at each transverse location within each slab, assigning a single value representative of the intensity across the thickness of the slab;
    for each slab, generating a 2-D image composed of the single representative intensity values at each of the transverse locations; and
    displaying the generated 2-D images automatically in sequence.

6. A method as recited in claim 5, wherein one or both of the boundaries are identified by segmenting layers in the retina.

7. A method as recited in claim 6, wherein one of the boundaries is the RPE.

8. A method as recited in claim 5, wherein at least one of the slabs is conformal to the photoreceptor layer.

9. A method as recited in claim 5, wherein at least one of the slabs is conformal to the ILM.

10. A method as recited in claim 5, wherein the sequential display of the images takes less than 5 seconds.

11. A method as recited in claim 5, wherein the sequential display of the images takes less than 2 seconds.

12. A method as recited in claim 5, wherein the slabs are of non-uniform thickness.

13. A method as recited in claim 5, further comprising overlaying an additional image on the generated images.

14. A method as recited in claim 13, wherein the additional image is a blood vessel map.

15. A method as recited in claim 5, wherein the boundaries are pre-set in the OCT system.

16. A method as recited in claim 5, wherein the boundaries are selected by the user.

17. A method as recited in claim 5, wherein the single value is the integrated intensity for that region.

18. A method as recited in claim 5, wherein the single value is the sum of the reflected intensities for that region.

19. A method as recited in claim 5, further comprising simultaneously displaying one or more B-scans along with the generated 2D images, wherein indicia on the generated 2D images indicates the location of the B-scan data that is displayed.

20. A method as recited in claim 19, wherein the indicia can be adjusted based on input from the user and the B-scans being displayed will be adjusted accordingly.

21. A method as recited in claim 5, wherein the display of the images is used as a navigation aid to determine locations for further data acquisition.

22. A method as recited in claim 5, further comprising repeating the defining, dividing, assigning, generating and displaying steps for a second set of boundaries within the 3-D data set.

23. A method as recited in claim 5 wherein the region is divided into at least five slabs and at least five different images are displayed in sequence.

24. A system for collecting and displaying optical coherence tomography (OCT) image data comprising:
    a light source arranged to generate a beam of radiation;
    a beam divider for separating the beam along a sample and reference arm;
    optics for scanning the beam in the sample arm over a set of transverse locations on a sample;
    a detector for measuring light returning from the sample and the radiation returning from the reference arm, and generating a set of output signals in response thereto;
    a display; and a processor for converting the set of output signals into 3D OCT image data, said processor defining a region of data between two spaced apart boundaries within the 3D data and dividing the region into a plurality of slabs of data extending between the boundaries, said processor assigning a single value representative of the intensity across the thickness of the slab for each transverse location in the slab, said processor generating a 2-D image for each slab composed of the single representative intensity values at each of the transverse locations and causing said generated 2-D to be sequentially displayed on said display.

25. A system as recited in claim 24 wherein at least one of the boundaries corresponds to a physical surface within the sample.

* * * * *

UNITED STATES PATENT AND TRADEMARK OFFICE
CERTIFICATE OF CORRECTION

PATENT NO. : 8,944,597 B2
APPLICATION NO. : 13/740875
DATED : February 3, 2015
INVENTOR(S) : Scott A. Meyer et al.

It is certified that error appears in the above-identified patent and that said Letters Patent is hereby corrected as shown below:

Title Page, item (56),

On page 2, in column 2, under "Other Publications", line 3, delete "Investigatative" and insert -- Investigative --, therefor.

On page 3, in column 2, under "Other Publications", line 10, delete "Opthalmoscopy," and insert -- Ophthalmoscopy, --, therefor.

In the Specification,

In column 3, line 12, delete "2006)" and insert -- 2006). --, therefor.

Signed and Sealed this
Ninth Day of June, 2015

Michelle K. Lee
*Director of the United States Patent and Trademark Office*